United States Patent
Yokota et al.

(10) Patent No.: US 8,189,898 B2
(45) Date of Patent: May 29, 2012

(54) GENE EXPRESSION IMAGE CONSTRUCTING METHOD AND GENE EXPRESSION IMAGE CONSTRUCTING SYSTEM

(75) Inventors: Hideo Yokota, Saitama (JP); Yuko Oho, Yokohama (JP); Kazuro Shimokawa, Yokohama (JP)

(73) Assignee: Riken, Wako-shi (JP)

( * ) Notice: Subject to any disclaimer, the term of this patent is extended or adjusted under 35 U.S.C. 154(b) by 1087 days.

(21) Appl. No.: 12/065,014

(22) PCT Filed: Aug. 29, 2006

(86) PCT No.: PCT/JP2006/316997
§ 371 (c)(1),
(2), (4) Date: Apr. 7, 2008

(87) PCT Pub. No.: WO2007/026705
PCT Pub. Date: Mar. 8, 2007

(65) Prior Publication Data
US 2010/0150414 A1    Jun. 17, 2010

(30) Foreign Application Priority Data
Aug. 29, 2005   (JP) .................................. 2005-248312

(51) Int. Cl.
*G06K 9/00* (2006.01)
(52) U.S. Cl. ...................................................... 382/133
(58) Field of Classification Search .................. 382/129, 382/133
See application file for complete search history.

(56) References Cited

U.S. PATENT DOCUMENTS
6,245,517 B1 * 6/2001 Chen et al. ........................ 506/3
(Continued)

FOREIGN PATENT DOCUMENTS
JP   2002-085094 A   3/2002
(Continued)

OTHER PUBLICATIONS
Brown et al., Physiological Genomics, vol. 8, pp. 159-167, Jan. 2002.*
(Continued)

*Primary Examiner* — W. B. Perkey
(74) *Attorney, Agent, or Firm* — Foley & Lardner LLP

(57) ABSTRACT

The present invention aims to provide a gene expression image constructing method and a gene expression image constructing system being able to three-dimensionally show expression patterns of a vastly larger number of genes (specifically, about 30,000 genes). In the present invention, a sample is cut, images of sections of the cut sample are picked up and a stereoscopic image of sample, which is a three-dimensional image of the sample, is constructed based on a plurality of picked-up section images, the amount of expression of genes present in the sample is measured based on a plurality of slices prepared when the sample is cut, and a gene expression image in which an expression state of genes present in the sample and a stereoscopic image of sample are associated with each other is constructed based on a predetermined image reconstruction technique from the constructed stereoscopic image of sample and the measured amount of expression.

12 Claims, 6 Drawing Sheets

U.S. PATENT DOCUMENTS

| | | | |
|---|---|---|---|
| 6,326,146 B1 * | 12/2001 | O'Dell et al. ................... 435/6 |
| 6,528,279 B2 | 3/2003 | Yokota et al. |
| 6,587,706 B1 * | 7/2003 | Viswanathan ................ 600/410 |
| 7,003,440 B2 | 2/2006 | Gojobori et al. |
| 2002/0058300 A1 | 5/2002 | Yokota et al. |
| 2002/0150941 A1 | 10/2002 | Gojobori et al. |
| 2003/0215121 A1 | 11/2003 | Yokota et al. |
| 2005/0107961 A1 | 5/2005 | Uemura et al. |
| 2007/0141613 A1 * | 6/2007 | Daghighian ................... 435/6 |

FOREIGN PATENT DOCUMENTS

| | | |
|---|---|---|
| JP | 2002-148153 A | 5/2002 |
| JP | 2003-242154 A | 8/2003 |
| JP | 2003-254902 A | 9/2003 |
| JP | 2003-254964 A | 9/2003 |

OTHER PUBLICATIONS

J. Sharpe et al., "Optical Projection Tomography as a Tool for 3D Microscopy and Gene Expression Studies," Science, vol. 296, Apr. 19, 2002, pp. 541-545.

J. Streicher et al., "Computer-based three-dimensional visualization of developmental gene expression," Nature Genetics, vol. 25, Jun. 2000, pp. 147-152.

H. Yokota et al., "Development of observation technique of three dimensional localization of expressed gene in the hole body," Bioimaging, vol. 11, No. 3, 1998, pp. 155-156 with English translation pp. 1-5.

H. Yokota et al., "Development of 3-Dimensional Internal Structure Microscope (3D-ISM) for Observation of Expressed Gene," Japanese Journal of Medical Electronics and Biological Engineering, vol. 36, No. 3, pp. 244-251 with English translation pp. 1-14.

S. Iwasaki et al., "New CT Image Reconstruction Algorithm Based on the Bayes Estimation," Nuclear Instruments and Methods in Physics Research, A422, (1999), pp. 683-687.

H. Kudo, "Iterative Methods for Tomographic Image Reconstruction: Foundations and Surprising Examples," Medical Imaging Technology, vol. 23, No. 1, Jan. 2005, pp. 23-25, with English translation pp. 1-6.

* cited by examiner

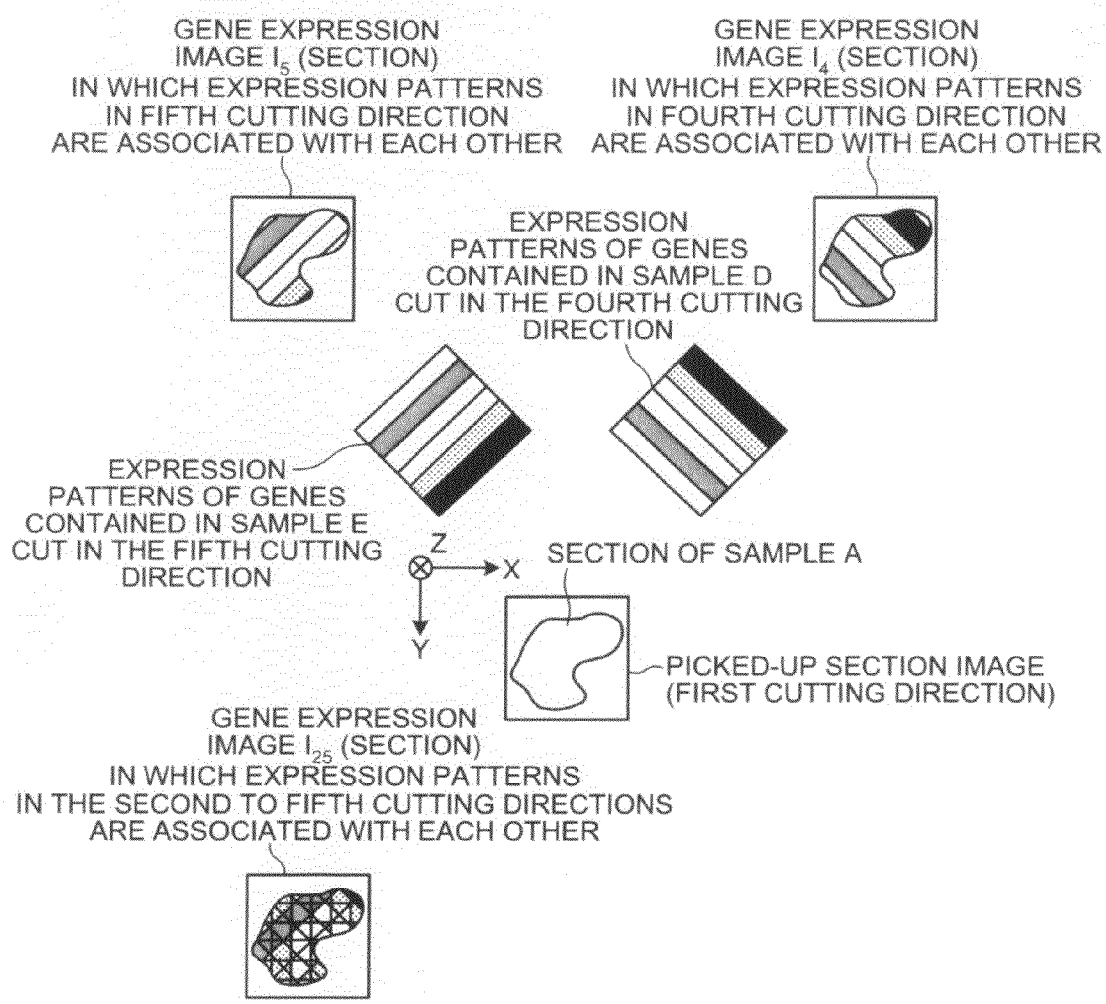

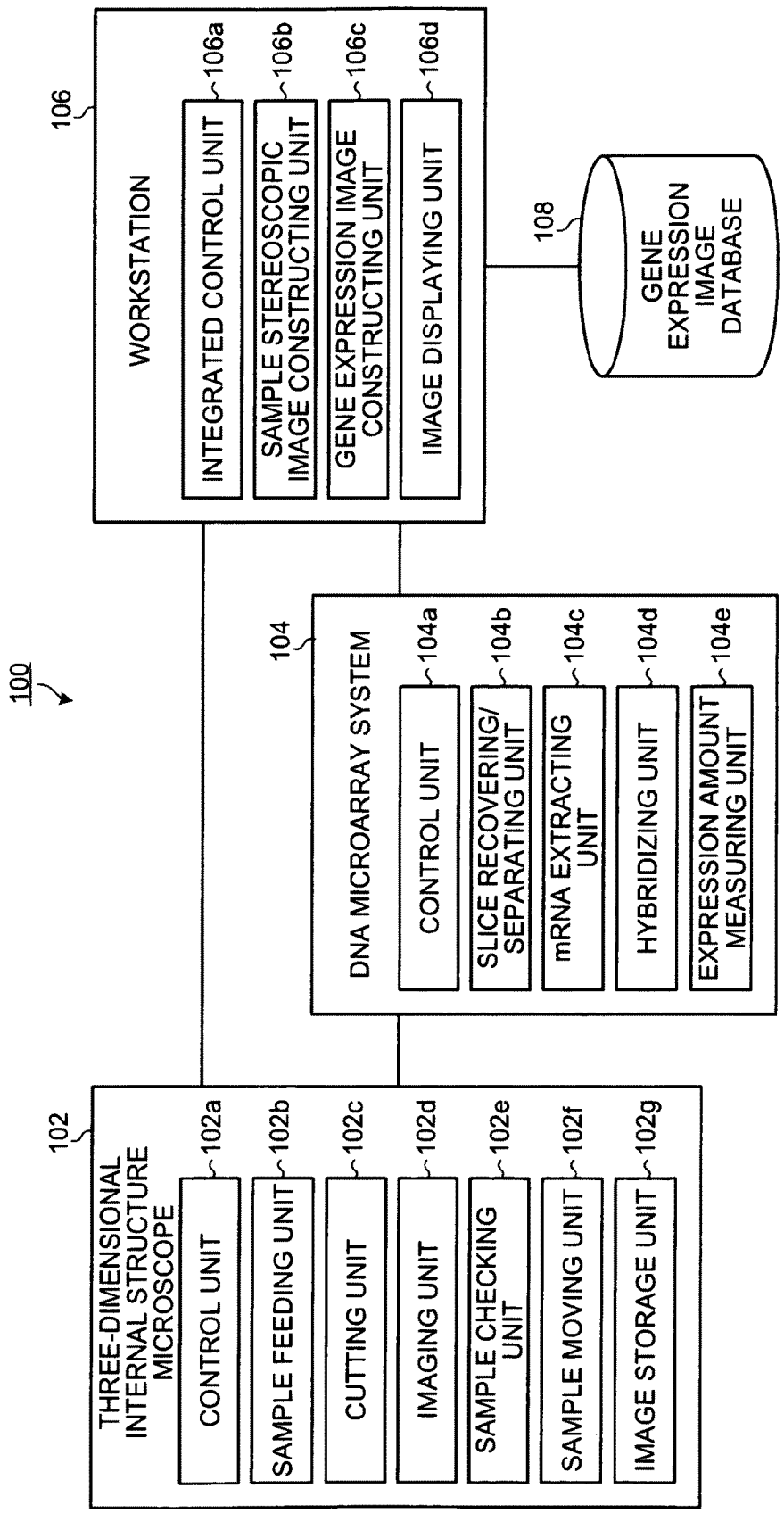

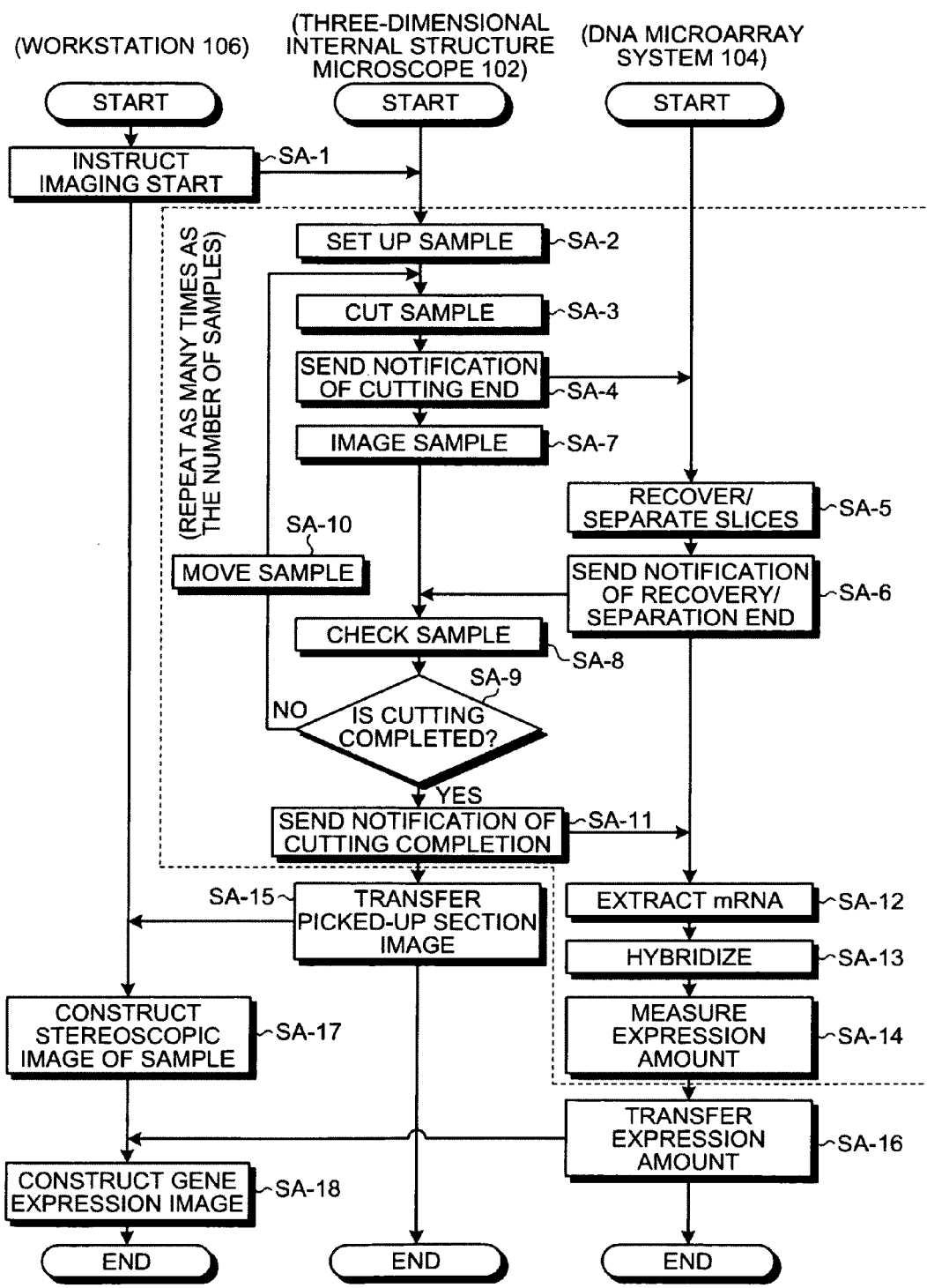

GENE EXPRESSION IMAGE CONSTRUCTING METHOD AND GENE EXPRESSION IMAGE CONSTRUCTING SYSTEM

TECHNICAL FIELD

The present invention relates to a gene expression image constructing method for constructing a gene expression image in which an expression state (expression pattern) of genes present in a sample and a stereoscopic image of sample, which is a three-dimensional image of the sample, are associated with each other, and a gene expression image constructing system.

BACKGROUND ART

Patent Document 1 and Patent Document 2 disclose technologies for three-dimensionally observing localization of a gene (expressed gene), that is, an expression pattern of a gene, expressed in a biological material such as an animal or a plant.

In Patent Document 1, a technology for three-dimensionally observing of biological material based on images picked up for each cut surface by successively cutting the genetically modified biological material having a marker (such as a fluorescent material and scintillating material) detectable when a specific gene is expressed and picking up section images, which are images of a cut surface, each time the biological material is cut is explained. This makes it possible to make a whole biological material an observational target and to observe three-dimensional localization of expressed genes in the biological material.

In Patent Document 2, a technology for three-dimensionally observing genetically modified biological material based on picked-up two-dimensional images by sequentially squeezing out the genetically modified biological material having a marker (such as a fluorescent material and scintillating material) detectable when a specific gene is expressed in a fixed direction, condensing light on a section of the squeezed-out genetically modified biological material, and picking up two-dimensional images of the section using a reflected light from the section where the light is condensed. This makes it possible to make a whole biological material an observational target region and to observe three-dimensional localization of an expressed gene in a microscopic region (a region of the size of a cell) in the observation target region.

DNA microarray technology for analyzing expression patterns of genes present in a living being, as exemplified by GeneChip (registered trademark) manufactured by Affymetrix and OligoDNA Microarray manufactured by Agilent Technologies, has been developed. Currently, DNA chips for analyzing expression patterns of about 30,000 genes are under development.

Patent Document 1: JP-A-2003-254902
Patent Document 2: JP-A-2003-254964

DISCLOSURE OF INVENTION

Problem to be Solved by the Invention

However, according to the technology described in Patent Document 1 or Patent Document 2, there is a problem that expression patterns of genes are three-dimensionally shown via a marker (such as a fluorescent material and scintillating material) embedded in a biological material and detectable when specific genes are expressed and therefore, the number of target genes is limited to a small number ranging from one to five.

The present invention has been developed in view of the above problem and an object thereof is to provide a gene expression image constructing method and a gene expression image constructing system capable of three-dimensionally showing expression patterns of a vastly larger number of genes than the above number.

Means for Solving Problem

To achieve the above objects, one aspect of the present invention is a gene expression image constructing method for constructing a gene expression image in which an expression state of genes present in a sample and a stereoscopic image of the sample are associated with each other. The gene expression image constructing method according to one aspect of the present invention includes a cutting step of cutting the sample, and a sample stereoscopic image construction step of picking up images of sections of the sample cut at the cutting step and constructing the stereoscopic image of the sample which is a three-dimensional image of the sample, based on a plurality of picked-up section images. The gene expression image constructing method according to one aspect of the present invention further includes an expression amount measurement step of measuring an amount of expression of the genes present in the sample based on a plurality of slices prepared when the sample is cut at the cutting step, and a gene expression image construction step of constructing the gene expression image based on a predetermined image reconstruction technique from the stereoscopic image of the sample constructed at the sample stereoscopic image construction step and the amount of expression measured at the expression amount measurement step.

Another aspect of the present invention is the gene expression image constructing method, wherein a plurality of the samples is prepared, the cutting step, the sample stereoscopic image construction step, and the expression amount measurement step are performed for each of the sample in a direction preset for each of the sample, and at the gene expression image construction step, the gene expression image is constructed based on the predetermined image reconstruction technique from the stereoscopic image of the sample constructed at the sample stereoscopic image construction step for each of the sample and the amount of expression measured at the expression amount measurement step for each of the sample.

Still another aspect of the present invention is the gene expression image constructing method, wherein the sample stereoscopic image construction step, further includes a region section image extraction step of recognizing a region preset for each picked-up section image from each of the picked-up section images and extracting a section image of region which is a section image of the recognized region, and a region stereoscopic image construction step of constructing a stereoscopic image of region which is a three-dimensional image constructed of a plurality of regions recognized at the region section image extraction step based on a plurality of region section images extracted at the region section image extraction step, wherein at the sample stereoscopic image construction step, the stereoscopic image of region is constructed as a stereoscopic image of the sample.

Still another aspect of the present invention is the gene expression image constructing method, wherein the gene expression image construction step, further includes an expression amount correction step of calculating an area of the preset region based on the region section image extracted at the region section image extraction step and correcting the amount of expression measured at the expression amount measurement step based on the calculated area, and a corrected expression image construction step of constructing the gene expression image based on the predetermined image reconstruction technique from the stereoscopic image of region constructed at the region stereoscopic image construction step and the amount of expression corrected at the expression amount correction step.

Still another aspect of the present invention is the gene expression image constructing method, wherein at the expression amount measurement step, the amount of expression of genes is measured and also reliability information which is information on reliability of the measured amount of expression is calculated, and at the gene expression image construction step, the gene expression image is constructed based on the predetermined image reconstruction technique from the stereoscopic image of sample constructed at the sample stereoscopic image construction step and the amount of expression measured and the reliability information calculated at the expression amount measurement step.

Still another aspect of the present invention is the gene expression image constructing method, wherein an analytic technique or an approximate solution estimation technique is used as the predetermined image reconstruction technique.

The present invention also relates to a gene expression image constructing system. One aspect of the present invention is the gene expression image constructing system that constructs a gene expression image in which an expression state of genes present in a sample and a stereoscopic image of the sample are associated with each other. The gene expression image constructing system according to one aspect of the present invention includes a cutting unit that cuts the sample, and a sample stereoscopic image construction unit that picks up images of sections of the sample cut by the cutting unit and constructs the stereoscopic image of the sample which is a three-dimensional image of the sample, based on a plurality of picked-up section images. The gene expression image constructing system according to one aspect of the present invention further includes an expression amount measurement unit that measures an amount of expression of the genes present in the sample based on a plurality of slices prepared when the sample is cut by the cutting unit, and a gene expression image construction unit that constructs the gene expression image based on a predetermined image reconstruction technique from the stereoscopic image of the sample constructed by the sample stereoscopic image construction unit and the amount of expression measured by the expression amount measurement unit.

Another aspect of the present invention is the gene expression image constructing system, wherein a plurality of the samples is prepared, the cutting unit, the sample stereoscopic image construction unit, and the expression amount measurement unit are performed for each of the sample in a direction preset for each of the sample, and at the gene expression image construction unit, the gene expression image is constructed based on the predetermined image reconstruction technique from the stereoscopic image of the sample constructed by the sample stereoscopic image construction unit for each of the sample and the amount of expression measured by the expression amount measurement unit for each of the sample.

Still another aspect of the present invention is the gene expression image constructing system, wherein the sample stereoscopic image construction unit, further includes a region section image extraction unit that recognizes a region preset for each picked-up section image from each of the picked-up section images and extracting a section image of region which is a section image of the recognized region, and a region stereoscopic image construction unit that constructs a stereoscopic image of region which is a three-dimensional image constructed of a plurality of regions recognized by the region section image extraction unit based on a plurality of region section images extracted by the region section image extraction unit, wherein at the sample stereoscopic image construction unit, the stereoscopic image of region is constructed as a stereoscopic image of the sample.

Still another aspect of the present invention is the gene expression image constructing system, wherein the gene expression image construction unit, further includes an expression amount correction unit that calculates an area of the preset region based on the region section image extracted by the region section image extraction unit and corrects the amount of expression measured by the expression amount measurement unit based on the calculated area, and a corrected expression image construction unit that constructs the gene expression image based on the predetermined image reconstruction technique from the stereoscopic image of region constructed by the region stereoscopic image construction unit and the amount of expression corrected by the expression amount correction unit.

Still another aspect of the present invention is the gene expression image constructing system, wherein at the expression amount measurement unit, the amount of expression of genesis measured and also reliability information which is information on reliability of the measured amount of expression is calculated, and at the gene expression image construction unit, the gene expression image is constructed based on the predetermined image reconstruction technique from the stereoscopic image of sample constructed by the sample stereoscopic image construction unit and the amount of expression measured and the reliability information calculated by the expression amount measurement unit.

Still another aspect of the present invention is the gene expression image constructing system, wherein an analytic technique or an approximate solution estimation technique is used as the predetermined image reconstruction technique.

EFFECT OF THE INVENTION

According to a gene expression image constructing method and a gene expression image constructing system of the present invention, (1) a sample is cut, (2) images of sections of the cut sample are picked up and a stereoscopic image of sample, which is a three-dimensional image of the sample, is constructed based on a plurality of picked-up section images, (3) the amount of expression of genes present in the sample is measured based on a plurality of slices prepared when the sample is cut, and (4) a gene expression image in which an expression state of genes present in the sample and a stereoscopic image of sample are associated with each other is constructed based on a predetermined image reconstruction technique from the constructed stereoscopic image of sample and the measured amount of expression. Accordingly, an effect of being able to three-dimensionally show expression patterns of a vastly larger number of genes (specifically, about 30,000 genes) is achieved. In other words, an effect of being able to three-dimensionally reveal localization and the amount of expression of a vastly larger number of expression patterns than that in the conventional art in the sample is achieved. In addition, information about interactions between genes (expressed genes) expressed in the sample can be obtained from the above effect.

Also, according to a gene expression image constructing method and a gene expression image constructing system of the present invention, a plurality of samples is prepared and the above (1), (2), and (3) are performed for each sample in a cutting direction preset for each sample (e.g. cutting directions orthogonal to each other) to construct a gene expression image based on a predetermined image reconstruction technique from a constructed stereoscopic image of each sample and a measured amount of expression of each sample in the above (4). Accordingly, an effect of being able to finely show expression patterns of genes on a gene expression image is achieved. In other words, an effect of being able to improve spatial resolution of expression patterns of genes on a gene expression image is achieved. That is, an effect of being able to improve precision of mapping of expression patterns of genes shown on a gene expression image is achieved.

Also, according to a gene expression image constructing method and a gene expression image constructing system of the present invention, in the above (2), (2-1) a region preset for each picked-up section image is recognized from each of the picked-up section images and a region section image, which is a section image of the recognized region, is extracted, and (2-2) a stereoscopic image of region, which is a three-dimensional image constructed of a plurality of recognized regions, is constructed based on a plurality of extracted region section images as a stereoscopic image of sample. More specifically, for example, by excluding regions in which there is no gene from each picked-up section image (for example, a region near the sample and a region where it is known that a target gene will not be expressed), region section images of a region of interest (for example, a region where a target gene is present or a tissue region) are extracted and a stereoscopic image of region is constructed based on a plurality of extracted region section images. Accordingly, an effect of being able to three-dimensionally show expression patterns of genes on a gene expression image in which a desired stereoscopic image of region and an expression state of genes are associated with each other is achieved. Also, according to the present invention, an effect of being able to improve spatial resolution of expression patterns of genes on a gene expression image constructed in the end is achieved because when extracting a desired stereoscopic image of region, for example, expression sites of genes can be limited.

Also, according to a gene expression image constructing method and a gene expression image constructing system of the present invention, in the above (4), (4-1) an area of a preset region is calculated based on the region section image extracted in the above (2-1) and the measured amount of expression is corrected based on the calculated area, and (4-2) a gene expression image is constructed based on a predetermined image reconstruction technique from the stereoscopic image of region constructed in the above (2-2) and the amount of expression corrected in the above (4-1). Accordingly, an effect of being able to improve precision of the value of the amount of expression shown on a gene expression image is achieved. Also, an effect of being able to show the amount of expression per unit area on a gene expression image is achieved.

Also, according to a gene expression image constructing method and a gene expression image constructing system of the present invention, in the above (3), the amount of expression of genes is measured and also reliability information, which is information on reliability of the measured amount of expression, is calculated and, in the above (4), a gene expression image is constructed based on a predetermined image reconstruction technique from a constructed stereoscopic image of sample (for example, a stereoscopic image of region), the measured amount of expression (for example, the corrected amount of expression), and the calculated reliability information. Accordingly, an effect of being able to increase reliability of expression patterns of genes shown on a gene expression image is achieved.

Further, according to a gene expression image constructing method and a gene expression image constructing system of the present invention, an analytic technique or an approximate solution estimation technique is used as a predetermined image reconstruction technique. Accordingly, an effect of being able to construct a gene expression image using an existing technique is achieved.

BRIEF DESCRIPTION OF DRAWINGS

FIG. 5 is a diagram for explaining an example of the technique for constructing a gene expression image for five samples (Sample A, Sample B, Sample C, Sample D, and sample E);

FIG. 6 is a block diagram for explaining a configuration of a gene expression image constructing system 100; and FIG. 7 is a flow chart for explaining an example of processing performed by the gene expression image constructing system 100.

EXPLANATION OF LETTERS OR NUMERALS

Figure 1:
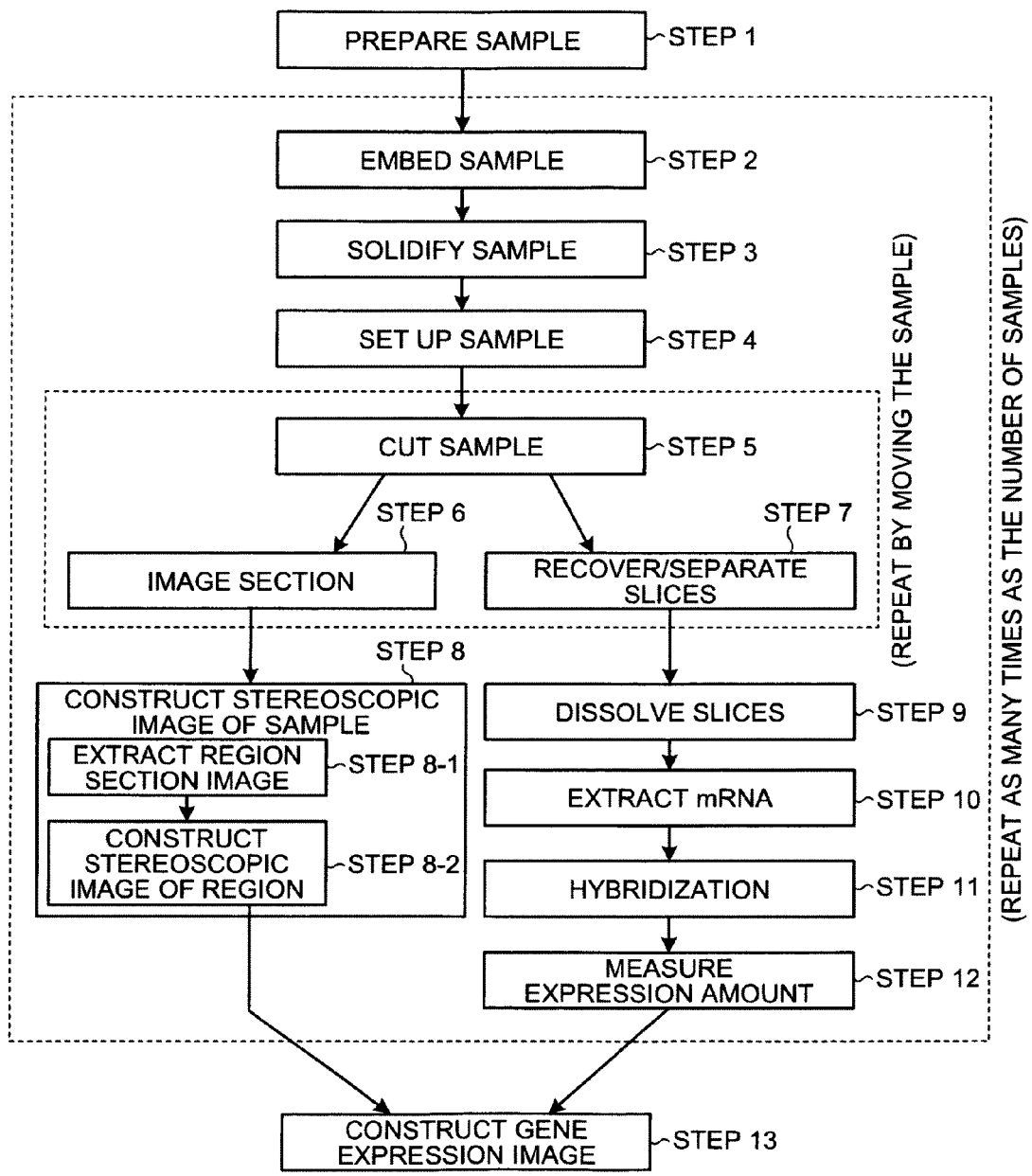
FIG. 1 is a diagram for explaining a basic principle of the present invention.

100 Gene expression image constructing system
102 Three-dimensional internal structure microscope
102a Control unit
102b Sample feeding unit
102c Cutting unit
102d Imaging unit
102e Sample checking unit
102f Sample moving unit
102g Image storage unit
104 DNA microarray system
104a Control unit
104b Slice recovering/separating unit
104c mRNA extracting unit
104d Hybridizing unit
104e Expression amount measuring unit
106 Workstation
106a Integrated control unit
106b Sample stereoscopic image constructing unit
106b1 Region section image extracting unit
106b2 Region stereoscopic image constructing unit
106c Gene expression image constructing unit
106c1 Expression amount correcting unit
106c2 Corrected expression image constructing unit
106d Image displaying unit
108 Gene expression image database

BEST MODE FOR CARRYING OUT THE INVENTION

An embodiment of a gene expression image constructing method and a gene expression image constructing system according to the present invention will be explained in detail below based on drawings. However, the present invention is not limited by the embodiment.

Basic Principle of the Present Invention

A basic principle of the present invention will be explained with reference to FIG. 1. FIG. 1 is a diagram for explaining the basic principle of the present invention. In the present invention, first a sample used for constructing a gene expression image is prepared (Step 1). Here, the sample has genes present therein and, more specifically, is a living body (individual) such as an animal or a plant, or an organ or the like contained in the living body. The number of samples to be prepared may be one or more. It is desirable to prepare a plurality of samples in which approximately the same genes are present to improve spatial resolution of expression patterns of genes shown on a gene expression image (in which an expression state of genes present in the sample and a stereoscopic image of sample, which is a three-dimensional image of the sample are associated with each other). Step 2 to Step 12 explained below are performed on one sample.

Next, in the present invention, the sample prepared in Step 1 is embedded (for example, frost embedding, paraffin embedding, and resin embedding) by an embedding agent by which mRNA is not deactivated (Step 2). Next, in the present invention, the sample embedded in Step 2 is solidified (for example, frozen, cooled, heated, or polymerized) (Step 3). Next, in the present invention, the sample solidified in Step 3 is set up at a setting position provided in a three-dimensional internal structure microscope at a predetermined angle (orientation) (Step 4). The predetermined angle (orientation) is an angle (orientation) used for cutting the sample in a cutting direction preset for each sample.

Figure 2:
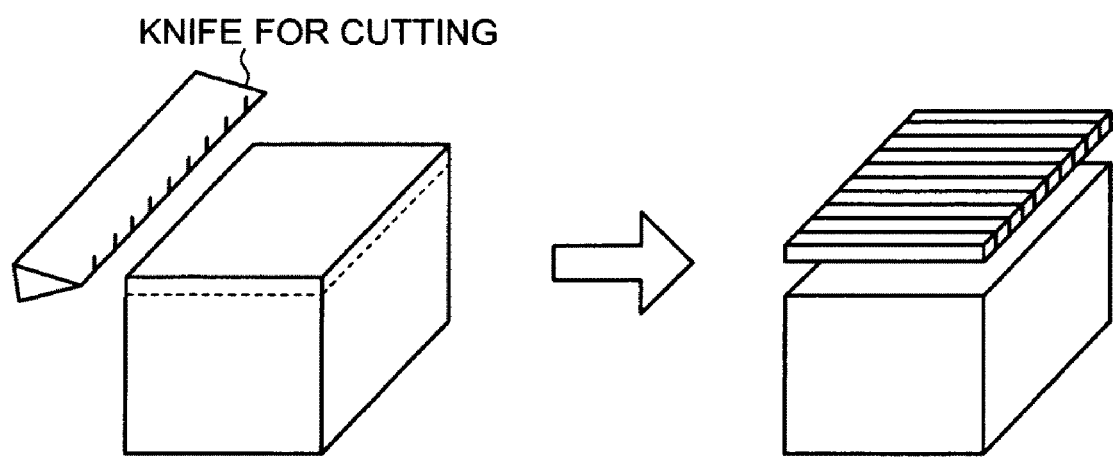
FIG. 2 is a diagram for explaining an example of a knife shape according to the present invention.
Figure 3:
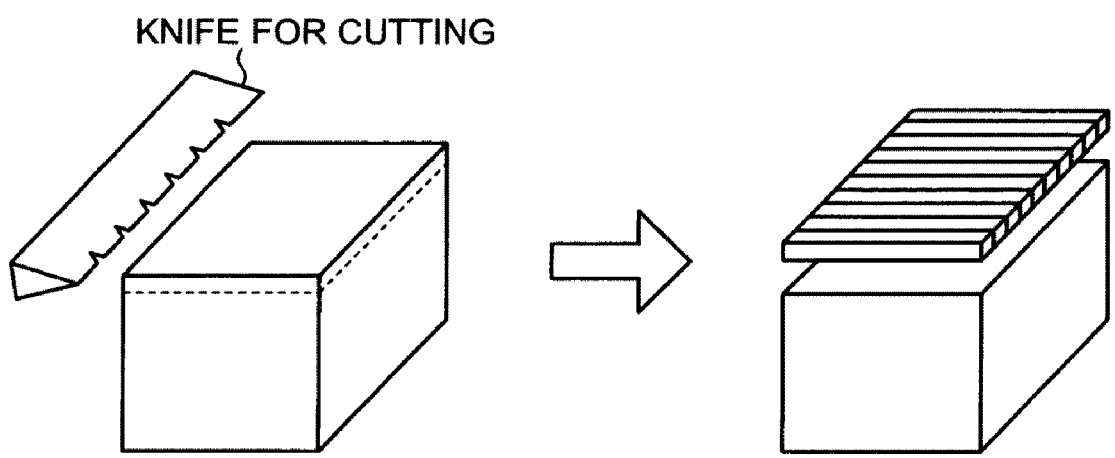
FIG. 3 is a diagram for explaining another example of the knife shape according to the present invention.

Next, in the present invention, the sample set up in Step 4 is cut to predetermined thickness by using a knife for cutting a sample provided in the three-dimensional internal structure microscope (Step 5). Here, the knife may have a shape (a shape with protrusions) shown in FIG. 2 or a shape (a shape with chipping) shown in FIG. 3. As shown in these figures, a plurality of strip slices can thereby be prepared by one cut. That is, strip slices whose two-dimensional direction is specified can be prepared from one sample. In other words, one sample can simultaneously be cut from two cutting directions. As a result, expression patterns of genes can finely be shown on a gene expression image constructed in the end. In other words, spatial resolution of expression patterns of genes shown on a gene expression image can be improved. Moreover, the number of samples to be prepared in Step 1 can thereby be reduced.

Next, in the present invention, a section of the sample cut in Step 5 is imaged by a CCD camera or a scanner set up at a predetermined position (Step 6). Here, in Step 6, a section may be imaged using a CCD camera by irradiating the section of the sample with white light, further to be imaged using the CCD camera by irradiating the section with a specific light (fluorescence). The section of the sample needs not be imaged each time the sample is cut in Step 6. For example, the section of the sample may be imaged each time after cutting the sample several times (for example, two or three times).

Also, in the present invention, in parallel with Step 6, slices prepared when the sample was cut in Step 5 are recovered using a predetermined container and also the number of collected slices is counted (Step 7). Here, in Step 7, when the number of recovered slices reached a predetermined number (for example, 100), the container containing as many recovered slices as the predetermined number is replaced with a new one. Slices recovered in Step 7 are thereby separated, for example, into a plurality of slice groups (slice groups whose location on the sample (stereoscopic image of sample) is known) consisting of a continuous predetermined number of slices (for example, about 100). In the present invention, section images picked up in Step 6 and slices prepared in Step 7 are managed by associating them. The number of slices contained in one slice group is changed when necessary in consideration of the volume of collected slices (product of the minimum number of slices and the cutting amount) and the limit of detection of mRNA.

Then, in the present invention, Step 5 to Step 7 are repeatedly performed until the sample is completely cut while moving the sample by a predetermined distance.

Next, in the present invention, a stereoscopic image of sample is constructed based on a plurality of section images picked up in Step 6 (Step 8). Here, in Step 8, a region (for example, a region where a target gene is present and a tissue region) preset for each picked-up section image may be recognized from each of the picked-up section images picked up in Step 6 to extract a region section image, which is a section image of the recognized region (Step 8-1), and to construct a stereoscopic image of region, which is a three-dimensional image consisting of a plurality of regions recognized in Step 8-1 based on a plurality of region section images extracted in Step 8-1 (Step 8-2).

Also, in the present invention, in parallel with Step 8, each of the slice groups separated in Step 7 is dissolved in a preservative liquid for each slice group (Step 9). Next, in the present invention, mRNA is extracted from each preservative liquid which has dissolved the slice group in Step 9 (Step 10). Next, in the present invention, mRNA extracted in Step 10 is hybridized with a DNA microarray (a microarray for analyzing gene expressions such as GeneChip (registered trademark) manufactured by Affymetrix and OligoDNA Microarray manufactured by Agilent Technologies) (Step 11). Next, in the present invention, a DNA microarray hybridized in Step 11 is scanned by a scanner (for example, a confocal laser scanner) and, based on scanned images, the amount of expression of genes contained in each slice group separated in Step 7 is measured (Step 12). Here, in Step 12, in addition to measurement of the amount of expression of genes, reliability information, which is information on reliability of the measured amount of expression, may be calculated. A known gene expression analysis technique is used for Step 9 to Step 12.

Then, in the present invention, Step 2 to Step 12 are repeatedly performed as many times as the number of samples prepared in Step 1.

Next, in the present invention, a gene expression image is constructed based on a predetermined image reconstruction technique from a stereoscopic image of sample constructed in Step 8 for each sample and the amount of expression measured in Step 12 for each sample (Step 13). In other words, a gene expression image is constructed by mapping the amount of expression onto the stereoscopic image of sample. More specifically, a gene expression image is constructed by plotting the value of the amount of expression measured based on slices of each sample cut in each cutting direction into a three-dimensional space (more specifically, a stereoscopic image of sample) as a potential (density) and estimating distribution of the amount of expression considered to be appropriate from the plotted amount of expression. Spatial resolution of a stereoscopic image of sample is far finer than that in a three-dimensional space of the amount of expression of genes corresponding to a slice group (more specifically, about 100 slices).

Here, in Step 13, a gene expression image for each sample may be constructed based on a predetermined image reconstruction technique from a stereoscopic image of sample constructed in Step 8 and the amount of expression measured in Step 12 to construct a gene expression image to be obtained in the end based on the constructed gene expression image corresponding to each constructed sample.

Also in Step 13, an area of a preset region extracted in Step 8-1 may be calculated based on the region section image extracted in Step 8-1 to correct the amount of expression measured in Step 12 based on the calculated area before constructing a gene expression image based on a predetermined image reconstruction technique from a stereoscopic image of region constructed in Step 8-2 and the corrected amount of expression.

Also in Step 13, a gene expression image may be constructed based on a predetermined image reconstruction technique from a stereoscopic image of sample (for example, stereoscopic image of region) constructed in Step 8 for each sample, the amount of expression (for example, the corrected amount of expression) measured in Step 12 for each sample, and calculated reliability information. Specifically, a gene expression image may be constructed by plotting the amounts of expression of genes contained in each slice group of each sample and measured by using each slice group corresponding to each sample cut in a predetermined cutting direction to a three-dimensional space (specifically, the stereoscopic image of sample) to construct a probability model of the amount of expression. More specifically, if cutting directions are, for example, three directions (x direction, y direction, and z direction) mutually intersecting at right angles, a gene expression image may be constructed by assuming that, for example, the ratio of contribution of the amount of expression in each direction is 33% and constructing a probability model of the amount of expression by multiplying the ratio of contribution by reliability information of each gene. Accordingly, an influence of the amount of expression of low reliability on expression patterns of genes shown on a gene expression image can be reduced. In other words, reliability of expression patterns of genes shown on a gene expression image can be improved. If GeneChip (registered trademark) manufactured by Affymetrix or OligoDNA Microarray manufactured by Agilent Technologies is used in Step 11, it is desirable to calculate, in addition to the amount of expression, reliability information about reliability of the amount of expression in Step 12 to further use the reliability information in Step 13.

An analytic method (See the document "S. Iwasaki, S. Odanaka, Y. Shintoku, M. Kitamura, M. Haruyama, M. Takase, K. Ara, "New CT image reconstruction algorithm based on the Bayes estimation", Nuclear Instruments and Methods in Physics Research, A422, pp. 683-687, 1999") or an approximate solution estimation technique (See the document, Hiroyuki Kudo, "Principles and Wonders of CT Image Reconstruction Method Using Successive Approximation", MEDICAL IMAGING TECHNOLOGY, Vol. 23, No. 1, January, 2005) may be used as a predetermined image reconstruction technique. When an analytic method is used, voxels of expression patterns of genes shown in a three-dimensional space (specifically, a gene expression image) can be made finer by making the imaging direction and cutting intervals (slice recovering pitch) finer. When an approximate solution estimation technique is used, expression patterns of genes shown on a gene expression image can statistically be estimated even with a relatively small number of imaging directions and relatively coarse cutting intervals (slice recovering pitch). The DNA microarray (particularly GeneChip (registered trademark) manufactured by Affymetrix and OligoDNA Microarray manufactured by Agilent Technologies) used in Step 11 can recently be purchased at a lower price than that in the conventional art, but is still expensive and using an approximate solution estimation technique in Step 13 is very effective in realizing the present invention inexpensively.

Figure 4:
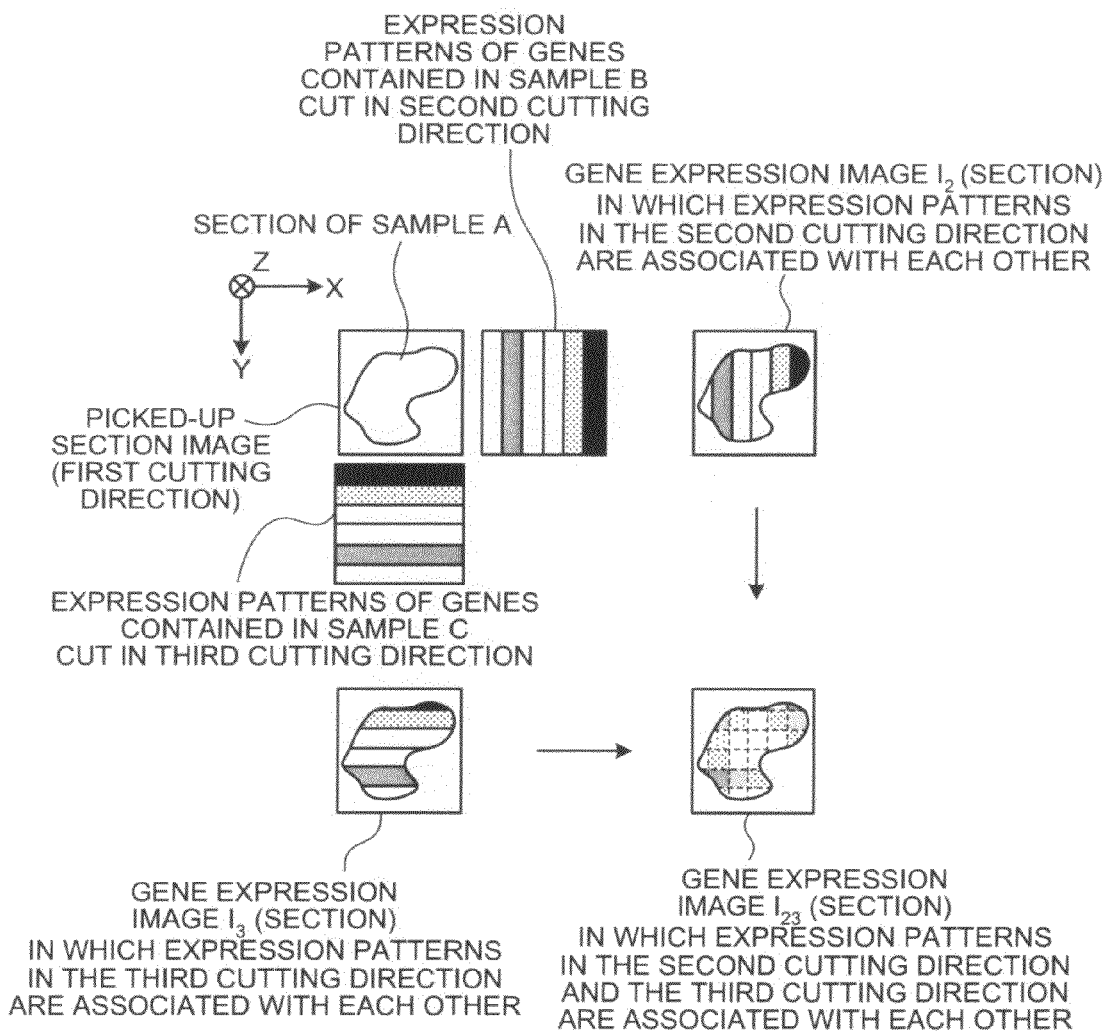
FIG. 4 is a diagram for explaining an example of a technique for constructing a gene expression image for three samples (Sample A, Sample B, and Sample C)

Here, an example of technique for constructing a gene expression image when three samples (Sample A, Sample B, and Sample C) are used and Sample A is cut in a first cutting direction, Sample B is cut in a second cutting direction, and Sample C is cut in a third cutting direction will conceptually be explained with reference to FIG. 4. The first cutting direction (as shown in FIG. 4, a direction perpendicular to the z axis), second cutting direction (as shown in FIG. 4, a direction perpendicular to the x axis), and third cutting direction (as shown in FIG. 4, a direction perpendicular to the y axis) are directions mutually intersecting at right angles. Approximately the same genes are present in Sample A, Sample B, and Sample C.

First, a gene expression image $I_2$ in which expression patterns in the second cutting direction are associated is constructed by associating expression patterns of genes contained in Sample B cut in the second cutting direction with each gene expression image containing a section of Sample A cut in the first cutting direction. Also, a gene expression image $I_3$ in which expression patterns in the third cutting direction are associated is constructed by associating expression patterns of genes contained in Sample C cut in the third cutting direction with each gene expression image containing a section of Sample A cut in the first cutting direction. Next, a gene expression image $I_{23}$ in which expression patterns in the second cutting direction and those in the third cutting direction are associated by superimposing the gene expression image $I_2$ and the gene expression image $I_3$.

To further improve spatial resolution of expression patterns of genes shown on the constructed gene expression image $I_{23}$, as shown in FIG. 5, Sample D and Sample E in which approximately the same genes are present as those in Sample A, Sample B, and sample C may further be added. Then, Sample D and Sample E are cut in a fourth cutting direction and a fifth cutting direction respectively, as shown in the figure, a gene expression image $I_4$ in which expression patterns in the fourth cutting direction are associated and a gene expression image $I_5$ in which expression patterns in the fifth cutting direction are associated are similarly constructed, and the gene expression image $I_4$, gene expression image $I_5$, and gene expression image $I_{23}$ are superimposed to construct a gene expression image $I_{25}$ in which expression patterns in the second to fifth cutting directions are associated.

The basic principle of the present invention has been explained, but in the present invention, observations (cutting and imaging) under a three-dimensional internal structure microscope and fluorescence observations of a sample in which a marker (fluorescent material) detectable when a specific gene is expressed is embedded (a sample dyed with the fluorescent material) may be combined. The amount of expressed genes (of any individual genes) in the sample can thereby be indicated on a gene expression image and further, relationships between conditions (activity) of expression of genes and types of expressed genes can be confirmed on the gene expression image. However, it is important to select the fluorescent dye used for dyeing so that the fluorescent wavelength of the fluorescent dye used for dyeing of expressed genes and that of the fluorescent dye used by the DNA microarray used in Step 11 do not overlap. A genetically modified organism designed to express fluorescence in all cells therein may also be applied. Extracorporeal portions such as digestive organs where there is no gene expression can thereby be revealed and, as a result, expression patterns of genes can be shown more clearly on a gene expression image.

System Configuration

The configuration of the gene expression image constructing system 100 according to the present invention will be explained with reference to FIG. 6. FIG. 6 is a block diagram for explaining the configuration of the gene expression image constructing system 100 and shows conceptually only a portion of the configuration that relates to the present invention.

As shown in FIG. 6, the gene expression image constructing system 100 is roughly configured by a three-dimensional internal structure microscope 102, a DNA microarray system 104, a workstation 106, and a gene expression image database 108, and these components are connected to be able to perform communication.

The three-dimensional internal structure microscope 102 has a function mainly of cutting samples to image sections of the cut samples. Based on input information (specifically, the sample number, number of images, temperature information, and sample replacement trigger) received from an integrated control unit 106a of the workstation 106 explained later, the three-dimensional internal structure microscope 102 outputs output information (specifically, picked-up section images (image information), and spatial resolution, cutting intervals, and light source information of the picked-up section images) and also produces slices. Specifically, the three-dimensional internal structure microscope 102 comprises a control unit 102a, a sample feeding unit 102b, a cutting unit 102c, an imaging unit 102d, a sample checking unit 102e, a sample moving unit 102f, and an image storage unit 102g.

The control unit 102a is, for example, a CPU for controlling overall operation of the three-dimensional internal structure microscope 102, has an internal memory for storing control programs such as an OS (Operating System), programs defining various kinds of procedures and required data, and performs information processing for performing various kinds of processing based on these programs. Based on information transferred from the workstation 106 and the DNA microarray system 104, the control unit 102a controls the sample feeding unit 102b, the cutting unit 102c, the imaging unit 102d, the sample checking unit 102e, the sample moving unit 102f, and the image storage unit 102g, and transfers information to the workstation 106 and the DNA microarray system 104. The control unit 102a includes a sequencer.

The sample feeding unit 102b prepares, embeds, solidifies, and sets up samples. The cutting unit 102c is, for example, a microtome and cuts a sample set up in a sample setup location provided in the three-dimensional internal structure microscope 102 at a predetermined angle (orientation) by a knife for cutting a sample.

The imaging unit 102d specifically includes a camera (for example, a CCD camera and a digital CCD camera), an image pickup tube, a photo multiplier, and a scanner, and images sections of samples cut by the cutting unit 102c. The image storage unit 102g is, for example, a memory device such as a RAM or ROM, a fixed disk device such as a hard disk, a flexible disk, an optical disk, videotape, or a photo film can be used.

The sample checking unit 102e checks the residual quantity of sample set up in the sample setup location provided in the three-dimensional internal structure microscope 102. The sample moving unit 102f moves a sample set up in the sample setup location provided in the three-dimensional internal structure microscope 102 by a predetermined distance. The image storage unit 102g stores section images picked up by the imaging unit 102d.

The DNA microarray system 104 has a function mainly of measuring the amount of expression of genes present in the sample based on a plurality of slices prepared when the sample is cut by the cutting unit 102c of the three-dimensional internal structure microscope 102. The DNA microarray system 104 recovers and separates slices based on the sample number, number of slices, slice recovery number, position information, and recovery trigger received from the integrated control unit 106a, and outputs the gene number, amount of expression, and reliability based on the sample number, number of slices, slice recovery number, position information, and DNA microarray number received from the integrated control unit 106a. Specifically, the DNA microarray system 104 comprises a control unit 104a, a slice recovering/separating unit 104b, an mRNA extracting unit 104c, a hybridizing unit 104d, and an expression amount measuring unit 104e.

The control unit 104a is, for example, a CPU for controlling overall operation of the DNA microarray system 104, has an internal memory for storing control programs such as an OS (Operating System), programs defining various kinds of procedures and required data, and performs information processing for performing various kinds of processing based on these programs. Based on information transferred from the workstation 106 and the three-dimensional internal structure microscope 102, the control unit 104a controls the slice recovering/separating unit 104b, the mRNA extracting unit 104c, the hybridizing unit 104d, and the expression amount measuring unit 104e, and transfers information to the workstation 106 and the three-dimensional internal structure microscope 102.

The slice recovering/separating unit 104b recovers slices when samples are cut by the cutting unit 102c of the three-dimensional internal structure microscope 102 and separates a plurality of recovered slices, for example, into a plurality of slice groups consisting of a continuous predetermined number (for example, about 100) of slices. The mRNA extracting unit 104c dissolves each slice group separated by the slice recovering/separating unit 104b in a preservative liquid for each slice group before extracting mRNA from each preservative liquid which has dissolved the slice group. The hybridizing unit 104d hybridizes mRNA extracted by the mRNA extracting unit 104c with the DNA microarray.

The expression amount measuring unit 104e scans the DNA microarray hybridized by the hybridizing unit 104d using a scanner and, based on a scanned image, measures the amount of expression of genes contained in each slice group separated by the slice recovering/separating unit 104b and also calculates reliability information, which is information about reliability of the measured amount of expression.

The workstation 106 mainly constructs a stereoscopic image of sample, which is a three-dimensional image of sample, based on a plurality of section images picked up by the imaging unit 102d of the three-dimensional internal structure microscope 102 and constructs a gene expression image in which an expression state (expression pattern) of genes present in a sample and a stereoscopic image of sample are associated with each other based on a predetermined image reconstruction technique from the constructed stereoscopic image of sample and the amount of expression measured by the expression amount measuring unit 104e of the DNA microarray system 104. Specifically, the workstation 106 comprises an integrated control unit 106a, a sample stereoscopic image constructing unit 106b, a gene expression image constructing unit 106c, and an image displaying unit 106d.

The integrated control unit 106a is, for example, a CPU for controlling overall operation of the whole system, has an internal memory for storing control programs such as an OS (Operating System), programs defining various kinds of procedures and required data, and performs information processing for performing various kinds of processing based on these programs. Based on information transferred from the three-dimensional internal structure microscope 102 and the DNA microarray system 104, the integrated control unit 106a controls the sample stereoscopic image constructing unit 106b, the gene expression image constructing unit 106c, and the image displaying unit 106d, and transfers information to the three-dimensional internal structure microscope 102 and the DNA microarray system 104.

The sample stereoscopic image constructing unit 106b constructs a stereoscopic image of sample, which is a three-dimensional image of sample, based on a plurality of section images picked up by the imaging unit 102d of the three-dimensional internal structure microscope 102. Based on input information (specifically, picked-up section images (image information), and spatial resolution, cutting intervals, and light source information of the picked-up section images) received from the three-dimensional internal structure microscope 102 and input information (specifically, the sample number, position information, number of images, and imaging time) received from the integrated control unit 106a, the sample stereoscopic image constructing unit 106b outputs output information (specifically, stereoscopic image of sample (three-dimensional image information), position information, and attribute information (such as tissue information)). Here, the sample stereoscopic image constructing unit 106b further comprises a region section image extracting unit 106b1 and a region stereoscopic image constructing unit 106b2. The region section image extracting unit 106b1 recognizes a region preset for each picked-up section image from each of the picked-up section images picked up by the imaging unit 102d of the three-dimensional internal structure microscope 102 and extracts a region section image, which is a section image of the recognized region. Based on a plurality of region section images extracted by the region section image extracting unit 106b1, the region stereoscopic image constructing unit 106b2 constructs a stereoscopic image of region, which is a three-dimensional image constructed of a plurality of regions recognized by the region section image extracting unit 106b1 as a stereoscopic image of sample.

The gene expression image constructing unit 106c constructs a gene expression image based on a predetermined image reconstruction technique from a stereoscopic image of sample constructed by the sample stereoscopic image constructing unit 106b, the amount of expression measured by the expression amount measuring unit 104e of the DNA microarray system 104, and calculated reliability information. Based on input information (specifically, stereoscopic image of sample (three-dimensional image information), position information, and attribute information (such as tissue information)) received from the sample stereoscopic image constructing unit 106b, input information (specifically, the sample number, number of slices, slice recovery number, position information, DNA microarray number, and processing conditions) received from the integrated control unit 106a, and input information (specifically, the gene number, amount of expression, and reliability) received from the DNA microarray system 104, the gene expression image constructing unit 106c outputs output information (specifically, the sample name, gene expression image (three-dimensional image), expressed gene information, and measurement conditions). Here, the gene expression image constructing unit 106c further comprises an expression amount correcting unit 106c1 and a corrected expression image constructing unit 106c2. The expression amount correcting unit 106c1 calculates, based on a region section image extracted by the region section image extracting unit 106b1, an area of a preset region and, based on the calculated area, corrects the amount of expression measured by the expression amount measuring unit 104e of the DNA microarray system 104. The corrected expression image constructing unit 106c2 constructs a gene expression image based on a predetermined image reconstruction technique from a stereoscopic image of region constructed by the region stereoscopic image constructing unit 106b2, the amount of expression corrected by the expression amount correcting unit 106c1, and calculated reliability information.

The image displaying unit 106d displays a stereoscopic image of sample constructed by the sample stereoscopic image constructing unit 106b and a gene expression image constructed by the gene expression image constructing unit 106c on a monitor. More specifically, the image displaying unit 106d displays a gene expression image in such a way that the value of the amount of expression of each gene shown on the gene expression image becomes visually recognizable.

The gene expression image database 108 stores a gene expression image constructed by the gene expression image constructing unit 106c of the workstation 106 together with information (specifically, the sample name, site name, gene expression information, measurement conditions and the like) concerning the gene expression image.

System Processing

Processing performed by the gene expression image constructing system 100 in the above configuration will be explained with reference to FIG. 7. FIG. 7 is a flow chart of an example of processing performed by the gene expression image constructing system 100. Here, an explanation of processing of sample preparation, that of sample embedding, and that of sample solidification is omitted.

First, the workstation 106 instructs the three-dimensional internal structure microscope 102 to start image pickup through processing of the integrated control unit 106a (step SA-1).

Next, after receiving an instruction from the workstation 106 through processing of the control unit 102a, the three-dimensional internal structure microscope 102 transfers the instruction to the sample feeding unit 102b and sets up a pre-solidified sample in a sample setup location provided, in the three-dimensional internal structure microscope 102 at a predetermined angle (orientation) through processing of the sample feeding unit 102b (step SA-2). The predetermined angle (orientation) is an angle (orientation) for cutting a sample at a cutting angle preset for each sample.

Next, the three-dimensional internal structure microscope 102 cuts the sample set up at step SA-2 to predetermined thickness using a knife provided in the three-dimensional internal structure microscope 102 through processing of the cutting unit 102c (step SA-3).

Next, the three-dimensional internal structure microscope 102 transfers a notification that sample cutting has been completed to the DNA microarray system 104 through processing of the control unit 102a (step SA-4).

Next, after receiving the notification that sample cutting has been completed transferred from the three-dimensional internal structure microscope 102 at step SA-4, the DNA microarray system 104 transfers the notification to the slice recovering/separating unit 104b through processing of the control unit 104a and recovers slices prepared when the sample is cut at step SA-3 using a predetermined container and also counts the number of recovered slices through processing of the slice recovering/separating unit 104b (step SA-5). Here, when the number of recovered slices reaches a predetermined number of slices (for example, 100) at step SA-5, the container in which as many slices as the predetermined number are contained is replaced with a new one through processing of the slice recovering/separating unit 104b. Slices recovered at step SA-5 are thereby separated, for example, into a plurality of slice groups (slice groups whose location on the sample is known) consisting of a continuous predetermined number of slices (for example, about 100).

Next, the DNA microarray system 104 transfers a notification that recovery/separation of slices has been completed to the three-dimensional internal structure microscope 102 through processing of the control unit 104a (step SA-6).

Subsequent to processing at step SA-4, the three-dimensional internal structure microscope 102, on the other hand, images a section of the sample cut at step SA-3 using a CCD camera set up at a predetermined position to convert the picked-up section image to digital data through processing of the imaging unit 102d (step SA-7). Here, at step SA-7, a section of the sample may be imaged using a CCD camera by irradiating the section with a white light, further to be imaged using a CCD camera by irradiating the section with a specific light (fluorescence).

Next, after receiving the notification transferred from the DNA microarray system 104 at step SA-6, the three-dimensional internal structure microscope 102 transfers the notification to the sample checking unit 102e through processing of the control unit 102a and checks the residual quantity of sample set up in the sample setup location in the three-dimensional internal structure microscope 102 through processing of the sample checking unit 102e (step SA-8).

Next, if sample cutting is not completed (step SA-9: No), the three-dimensional internal structure microscope 102 moves a sample by a predetermined distance through processing of the sample moving unit 102f (step SA-10) before returning to step SA-3. If sample cutting is completed (step SA-9: Yes), the three-dimensional internal structure microscope 102 transfers the notification that sample cutting has completed to the DNA microarray system 104 through processing of the control unit 102a (step SA-11).

Next, after receiving the notification transferred from the three-dimensional internal structure microscope 102 at step SA-11, the DNA microarray system 104 transfers the notification to the mRNA extracting unit 104c through processing of the control unit 104a and dissolves each slice group separated at step SA-5 in a preservative liquid for each slice group to extract mRNA from each preservative liquid which has dissolved the slice group through processing of the mRNA extracting unit 104c (step SA-12).

Next, the DNA microarray system 104 hybridizes mRNA extracted at step SA-12 with a DNA microarray (a microarray for analyzing gene expressions such as GeneChip (registered trademark) manufactured by Affymetrix and OligoDNA Microarray manufactured by Agilent Technologies) through processing of the hybridizing unit 104d (step SA-13).

Next, the DNA microarray system 104, through processing of the expression amount measuring unit 104e, scans the DNA microarray hybridized at step SA-13 by a scanner (for example, a confocal laser scanner) and, based on the scanned image, measures the amount of expression of genes contained in each slice group separated at step SA-5 and also calculates reliability information of the measured amount of expression (step SA-14).

Then, the gene expression image constructing system 100 repeatedly performs the processing from step SA-2 to step SA-14 as many times as the number of prepared samples.

Next, subsequent to processing at step SA-11, the three-dimensional internal structure microscope 102 transfers a plurality of section images (digitized picked-up section images) for each sample picked up at step SA-7 to the workstation 106 through processing of the control unit 102a (step SA-15).

The DNA microarray system 104, on the other hand, transfers, in parallel with processing at step SA-15, the amount of expression of genes contained in each slice group of each sample measured at step SA-14 and reliability information to the workstation 106 through processing of the control unit 104a (step SA-16).

Next, the workstation 106 receives the plurality of section images for each sample transferred from the three-dimensional internal structure microscope 102 at step SA-15 and the amount of expression of genes contained in each slice group of each sample and reliability information transferred from the DNA microarray system 104 at step SA-16 through processing of the integrated control unit 106a and constructs a stereoscopic image of sample based on the plurality of picked-up section images through processing of the sample stereoscopic image constructing unit 106b (step SA-17). Here, the sample stereoscopic image constructing unit 106b may construct a stereoscopic image of sample by recognizing a region (for example, a region where a target gene is present or a tissue region) preset for each picked-up section image from each picked-up section image picked up by the imaging unit 102d and extracting a section image of region, which is a section image of the recognized region, through processing of the region section image extracting unit 106b1 and constructing a stereoscopic image of region, which is a three-dimensional image constructed of a plurality of regions recognized by the region section image extracting unit 106b1 based on a plurality of region section images extracted by the region section image extracting unit 106b1 through processing of the region stereoscopic image constructing unit 106b2.

Next, the workstation 106 constructs a gene expression image based on a predetermined image reconstruction technique from a stereoscopic image of sample constructed at step SA-17 for each sample and the amount of expression of genes contained in each slice group of each sample and reliability information received at step SA-17 through processing of the gene expression image constructing unit 106c and stores the constructed gene expression image in the gene expression image database 108 through processing of the integrated control unit 106a (step SA-18). In other words, a gene expression image is constructed by mapping the amount of expression onto a stereoscopic image of sample in consideration of reliability information. More specifically, a gene expression image is constructed by plotting the value of the amount of expression onto a stereoscopic image of sample in consideration of reliability information as a potential (density) and estimating distribution of the amount of expression considered to be appropriate from the plotted amount of expression.

Here, the gene expression image constructing unit 106c may construct a gene expression image based on a predetermined image reconstruction technique, after calculating an area of a region (for example, a region where a target gene is present or a tissue region) preset for each picked-up section image based on a region section image extracted by the region section image extracting unit 106b1 and correcting the amount of expression received at step SA-17 based on the calculated area through processing of the expression amount correcting unit 106c1, from a stereoscopic image of region constructed by the region stereoscopic image constructing unit 106b2, the amount of expression corrected by the expression amount correcting unit 106c1, and reliability information received at step SA-17. Specifically, a gene expression image may be constructed by plotting the amount of expression of genes contained in each slice group of each sample onto a stereoscopic image of sample to construct a probability model of the amount of expression. More specifically, if cutting directions of sample are, for example, three directions (x direction, y direction, and z direction) mutually intersecting at right angles, a gene expression image may be constructed by assuming that, for example, the ratio of contribution of the amount of expression in each direction is 33% and constructing a probability model of the amount of expression by multiplying the ratio of contribution by reliability information of each gene.

An analytic method (See the document "S. Iwasaki, S. Odanaka, Y. Shintoku, M. Kitamura, M. Haruyama, M. Takase, K. Ara, "New CT image reconstruction algorithm based on the Bayes estimation", Nuclear Instruments and Methods in Physics Research, A422, pp. 683-687, 1999") or an approximate solution estimation technique (See the document, Hiroyuki Kudo, "Principles and Wonders of CT Image Reconstruction Method Using Successive Approximation", MEDICAL IMAGING TECHNOLOGY, Vol. 23, No. 1, January, 2005) may be used as a predetermined image reconstruction technique.

According to the gene expression image constructing system 100, as explained above, (1) a sample is cut, (2) images of sections of the cut sample are picked up and a stereoscopic image of sample, which is a three-dimensional image of the sample, is constructed based on a plurality of picked-up section images, (3) the amount of expression of genes present in the sample is measured based on a plurality of slices prepared when the sample is cut, and (4) a gene expression image in which an expression state of genes present in the sample and a stereoscopic image of sample are associated with each other is constructed based on a predetermined image reconstruction technique from the constructed stereoscopic image of sample and the measured amount of expression. Accordingly, expression patterns of a vastly larger number of genes (specifically, about 30,000 genes) than that in the conventional art can three-dimensionally be shown. In other words, localization and the amount of expression of a vastly larger number of expression patterns than that in the conventional art in the sample can three-dimensionally be revealed. Thereby, information about interactions between genes (expressed genes) expressed in the sample can be obtained.

So far, JP-A-2003-254902 or JP-A-2003-254964 has disclosed a technique of viewing three-dimensional localization of genes by marking one to five genes of interest from outside or of observing an expression profile of genes in a genetically modified organism. However, this technique allows only a small number of target genes ranging from one to five and thus, there is a limit to the number of target genes. On the other hand, a technique of analyzing expressed genes in a living organism, as exemplified by GeneChip (registered trademark) manufactured by Affymetrix and OligoDNA Microarray manufactured by Agilent Technologies, has been developed. Currently, a DNA chip for all expressed genes as many as about 30,000 has been developed. However, according to this technique, one chip analyzes gene expression patterns of only one sample and cannot know gene localization in a living organism. Such research is also required to reveal interactions between expressed genes.

Thus, using the gene expression image constructing system 100, expression patterns of a vastly larger number of genes (specifically, about 30,000 genes) than that in the conventional art can three-dimensionally be shown. In other words, localization and the amount of expression of a vastly larger number of expression patterns than that in the conventional art in the sample can three-dimensionally be revealed. Thereby, information about interactions between genes (expressed genes) expressed in the sample can be obtained.

Also, according to the gene expression image constructing system 100, a plurality of samples is prepared and the above (1), (2), and (3) are performed for each sample in a cutting direction preset for each sample (for example, cutting directions orthogonal to each other) to construct a gene expression image based on a predetermined image reconstruction technique from a constructed stereoscopic image of each sample and a measured amount of expression of each sample in the above (4). Accordingly, expression patterns of genes on a gene expression image can finely be shown. In other words, spatial resolution of expression patterns of genes on a gene expression image can be improved. That is, precision of mapping of expression patterns of genes shown on a gene expression image can be improved.

Also, according to the gene expression image constructing system 100, in the above (2), (2-1) a region preset for each picked-up section image is recognized from each of the picked-up section images and a region section image, which is a section image of the recognized region, is extracted, and (2-2) a stereoscopic image of region, which is a three-dimensional image constructed of a plurality of recognized regions, is constructed based on a plurality of extracted region section images as a stereoscopic image of sample. More specifically, for example, by excluding regions in which there is no gene from each picked-up section image (for example, a region near the sample and a region where it is known that a target gene will not be expressed), region section images of a region of interest (for example, a region where a target gene is present or a tissue region) are extracted and a stereoscopic image of region is constructed, based on a plurality of extracted region section images. Accordingly, expression patterns of genes can three-dimensionally be shown on a gene expression image in which a desired stereoscopic image of region and an expression state of genes are associated with each other. Also, according to the gene expression image constructing system 100, because when extracting a desired stereoscopic image of region, for example, expression sites of genes can be limited, spatial resolution of expression patterns of genes on a gene expression image constructed in the end can be improved.

Also, according to the gene expression image constructing system 100, in the above (4), (4-1) an area of a preset region is calculated based on the region section image extracted in the above (2-1) and the measured amount of expression is corrected based on the calculated area, and (4-2) a gene expression image is constructed based on a predetermined image reconstruction technique from the stereoscopic image of region constructed in the above (2-2) and the amount of expression corrected in the above (4-1). Accordingly, precision of the value of the amount of expression shown on a gene expression image can be improved. Also, the amount of expression per unit area on a gene expression image can be shown.

Also, according to the gene expression image constructing system 100, in the above (3), the amount of expression of genes is measured and also reliability information, which is information on reliability of the measured amount of expression, is calculated and, in the above (4), a gene expression image is constructed based on a predetermined image reconstruction technique from a constructed stereoscopic image of sample (for example, a stereoscopic image of region), the measured amount of expression (for example, the corrected amount of expression), and the calculated reliability information. Accordingly, reliability of expression patterns of genes shown on a gene expression image can be increased.

Also, according to the gene expression image constructing system 100, an analytic technique or an approximate solution estimation technique is used as a predetermined image reconstruction technique. Accordingly, a gene expression image can be constructed using an existing technique.

Industrial Applicability

A gene expression image constructing method and a gene expression image constructing system according to the present invention can construct, as explained above, a gene expression image in which an expression state (expression pattern) of genes present in a sample and a stereoscopic image of sample are associated with each other, which is a three-dimensional image of the sample, and is extremely useful for medical science, medicine manufacture, drug design, biological research, clinical laboratory tests and the like.

The invention claimed is:

1. A gene expression image constructing method for constructing a gene expression image in which an expression state of genes present in a sample and a stereoscopic image of the sample are associated with each other, the method comprising
   a cutting step of cutting a plurality of samples that represent said sample, wherein each of the plurality of samples is cut into sections in one direction such that at least two orthogonal directions are cut;
   a sample stereoscopic image construction step of picking up images of the sections of the plurality of samples cut at the cutting step and constructing the stereoscopic image of the sample which is a three-dimensional image of the sample, based on a plurality of the picked-up section images;
   an expression amount measurement step of measuring an amount of expression of the genes present in the sample corresponding to the picked-up section images based on a plurality of slices associated with the picked-up section images, prepared when the samples are cut at the cutting step; and
   a gene expression image construction step of constructing the gene expression image based on a predetermined image reconstruction technique from the stereoscopic image of the sample constructed at the sample stereoscopic image construction step and the amount of expression associated with the picked-up section images of each of the samples, measured at the expression amount measurement step.

2. The gene expression image constructing method according to claim 1, wherein
   at the cutting step, each of the samples is cut in a direction preset for each of the samples.

3. The gene expression image constructing method according to claim 1, wherein
   the sample stereoscopic image construction step, further includes:
   a region section image extraction step of recognizing a region preset for each picked-up section image from each of the picked-up section images and extracting a section image of region which is a section image of the recognized region, and
   a region stereoscopic image construction step of constructing a stereoscopic image of region which is a three-dimensional image constructed of a plurality of regions recognized at the region section image extraction step based on a plurality of region section images extracted at the region section image extraction step, wherein
   at the sample stereoscopic image construction step, the stereoscopic image of region is constructed as a stereoscopic image of the sample.

4. The gene expression image constructing method according to claim 3, wherein
   the gene expression image construction step, further includes:
   an expression amount correction step of calculating an area of the preset region based on the region section image extracted at the region section image extraction step and correcting the amount of expression associated with the picked-up section images of each of the samples, measured at the expression amount measurement step based on the calculated area, and
   a corrected expression image construction step of constructing the gene expression image based on the predetermined image reconstruction technique from the stereoscopic image of region of the samples, constructed at the region stereoscopic image construction step and the amount of expression associated with the picked-up section images of each of the samples, corrected at the expression amount correction step.

5. The gene expression image constructing method according to claim 1, wherein
   at the expression amount measurement step, the amount of expression of genes is measured and also reliability information which is information on reliability of the measured amount of expression is calculated, and
   at the gene expression image construction step, the gene expression image is constructed based on the predetermined image reconstruction technique from the stereoscopic image of the sample constructed at the sample stereoscopic image construction step and the amount of expression associated with the picked-up section images of each of the samples, measured and the reliability information calculated at the expression amount measurement step.

6. The gene expression image constructing method according to claim 1, wherein
   an analytic technique or an approximate solution estimation technique is used as the predetermined image reconstruction technique.

7. A gene expression image constructing system that constructs a gene expression image in which an expression state of genes present in a sample and a stereoscopic image of the sample are associated with each other, the system comprising
   a cutting unit that cuts a plurality of samples that represent said sample, wherein the cutting unit is capable of cutting the plurality of samples into sections in one direction such that at least two orthogonal directions are cut;
   a sample stereoscopic image construction unit that picks up images of sections of the samples cut by the cutting unit and constructs the stereoscopic image of the sample which is a three-dimensional image of the sample, based on a plurality of picked-up section images;
   an expression amount measurement unit that measures an amount of expression of the genes present in the sample corresponding to the picked-up section images based on a plurality of slices associated with the picked-up section images, prepared when the sample is cut by the cutting unit; and
   a gene expression image construction unit that constructs the gene expression image based on a predetermined image reconstruction technique from the stereoscopic image of the sample constructed by the sample stereoscopic image construction unit and the amount of expression associated with the picked-up section images of each of the samples, measured by the expression amount measurement unit.

8. The gene expression image constructing system according to claim 7, wherein the cutting unit cuts each of the samples in a direction preset for each of the samples.

9. The gene expression image constructing system according to claim 7, wherein
the sample stereoscopic image construction unit, further includes:
a region section image extraction unit that recognizes a region preset for each picked-up section image from each of the picked-up section images and extracting a section image of region which is a section image of the recognized region, and
a region stereoscopic image construction unit that constructs a stereoscopic image of region which is a three-dimensional image constructed of a plurality of regions recognized by the region section image extraction unit based on a plurality of region section images extracted by the region section image extraction unit, wherein
at the sample stereoscopic image construction unit, the stereoscopic image of region is constructed as a stereoscopic image of the sample.

10. The gene expression image constructing system according to claim 9, wherein
the gene expression image construction unit, further includes:
an expression amount correction unit that calculates an area of the preset region based on the region section image extracted by the region section image extraction unit and corrects the amount of expression associated with the picked-up section images of each of the samples, measured by the expression amount measurement unit based on the calculated area, and
a corrected expression image construction unit that constructs the gene expression image based on the predetermined image reconstruction technique from the stereoscopic image of region of the samples, constructed by the region stereoscopic image construction unit and the amount of expression associated with the picked-up section images of each of the samples, corrected by the expression amount correction unit.

11. The gene expression image constructing system according to claim 7, wherein
by the expression amount measurement unit, the amount of expression of genes is measured and also reliability information which is information on reliability of the measured amount of expression is calculated, and
by the gene expression image construction unit, the gene expression image is constructed based on the predetermined image reconstruction technique from the stereoscopic image of the sample constructed by the sample stereoscopic image construction unit and the amount of expression associated with the picked-up section images of each of the samples, measured and the reliability information calculated by the expression amount measurement unit.

12. The gene expression image constructing system according to claim 7, wherein
an analytic technique or an approximate solution estimation technique is used as the predetermined image reconstruction technique.

* * * * *